(12) United States Patent
Apostolakis et al.

(10) Patent No.: US 12,422,548 B2
(45) Date of Patent: Sep. 23, 2025

(54) SYSTEMS AND METHODS FOR GENERATING COLOR DOPPLER IMAGES FROM SHORT AND UNDERSAMPLED ENSEMBLES

(71) Applicant: KONINKLIJKE PHILIPS N.V., Eindhoven (NL)

(72) Inventors: Iason Zacharias Apostolakis, Cambridge, MA (US); Faik Can Meral, Mansfield, MA (US); Jun Seob Shin, Winchester, MA (US); Francois Guy Gerard Marie Vignon, Andover, MA (US); Shiying Wang, Melrose, MA (US); Jean-Luc Francois-Marie Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 238 days.

(21) Appl. No.: 18/010,008

(22) PCT Filed: Jun. 15, 2021

(86) PCT No.: PCT/EP2021/066014
§ 371 (c)(1),
(2) Date: Dec. 13, 2022

(87) PCT Pub. No.: WO2021/259694
PCT Pub. Date: Dec. 30, 2021

(65) Prior Publication Data
US 2023/0228873 A1    Jul. 20, 2023

Related U.S. Application Data

(60) Provisional application No. 63/042,602, filed on Jun. 23, 2020.

(51) Int. Cl.
*G01S 15/89* (2006.01)
*G01N 29/06* (2006.01)
*G01N 29/44* (2006.01)

(52) U.S. Cl.
CPC ...... *G01S 15/8988* (2013.01); *G01N 29/0654* (2013.01); *G01N 29/4481* (2013.01);
(Continued)

(58) Field of Classification Search
CPC ............ G01S 15/8979; G01S 15/8988; G01S 15/8915; G01S 15/8981; G01S 7/52026;
(Continued)

(56) References Cited

U.S. PATENT DOCUMENTS 6,443,896 B1    9/2002   Detmer
6,530,885 B1    3/2003   Entrekin et al.
(Continued)

FOREIGN PATENT DOCUMENTS

WO    2019166332 A1    9/2019
WO    2019222478 A1    11/2019
WO    2020083679 A1    4/2020

OTHER PUBLICATIONS

International Search Report and Written Opinion for PCT/EP2021/066014; Mailing date: Oct. 1, 2021, 8 pages.
(Continued)

*Primary Examiner* — Benjamin R Schmitt

(57) ABSTRACT

An ultrasound imaging system which acquires short and/or undersampled radiofrequency ensembles for generating color Doppler images. The ultrasound imaging system processes the short and/or undersampled ensembles to simulate color Doppler images acquired from long radiofrequency ensembles. In some examples, the ultrasound imaging system includes one or more neural networks to process the ensembles.

16 Claims, 14 Drawing Sheets

(52) U.S. Cl.
CPC ...... *G01S 15/8915* (2013.01); *G01S 15/8981* (2013.01); *G01N 29/0609* (2013.01)

(58) Field of Classification Search
CPC ............... G01N 29/06; G01N 29/0609; G01N 29/0645; G01N 29/0654; G01N 29/4481; A61B 8/488; A61B 8/5207; A61B 8/54; A61B 8/085
See application file for complete search history.

(56) References Cited

U.S. PATENT DOCUMENTS

| | | | | |
|---|---|---|---|---|
| 2003/0100833 A1* | 5/2003 | He | ........................ | G01S 7/5208 600/453 |
| 2019/0336033 A1* | 11/2019 | Takeshima | ........... | A61B 6/4241 |

OTHER PUBLICATIONS

Posada, D. et al., "Staggered Multiple-PRF Ultrafast Color Doppler", IEEE Transactions on Medical Imaging, 2016, vol. 35, No. 6, pp. 1510-1521.

Bonnefous, O. et al., "Time domain formulation of pulse-Doppler ultrasound and blood velocity estimation by cross correlation", Ultrason Imaging, 1986, vol. 8, p. 73-85.

Muth, S. et al., "Unsupervised dealiasing and denoising of color-Doppler data", Medical Image Analysis, 2011, vol. 15, pp. 577-588.

Wright, I.A. et al., "Neural network analysis of Doppler ultrasound blood flow signals: A pilot study", Ultrasound in Medicine & Biology, 1997, vol. 23, pp. 683-690.

Shahin, A. et al., "Cooperation of fuzzy segmentation operators for correction aliasing phenomenon in 3D color Doppler imaging", Artificial Intelligence in Medicine, 2000, vol. 19, pp. 121-154.

Dosovitskiy, A. et al., "FlowNet: Learning Optical Flow with Convolutional Networks", IEEE International Conference on Computer Vision (ICCV), 2015, pp. 2758-2766.

Van Sloun, R. J. G. et al., "Learning Doppler with Deep Neural Networks and its Application to Intra-Cardiac Echography", IEEE International Ultrasonics Symposium (IUS), 2018, pp. 1-4.

Krizhevsk, A. et al., "ImageNet Classification with Deep Convolutional Neural Networks", NIPS, 2012, 9 pages.

* cited by examiner

SYSTEMS AND METHODS FOR GENERATING COLOR DOPPLER IMAGES FROM SHORT AND UNDERSAMPLED ENSEMBLES

CROSS-REFERENCE TO PRIOR APPLICATIONS

This application is the U.S. National Phase application under 35 U.S.C. § 371 of International Application No. PCT/EP2021/066014, filed on Jun. 15, 2021, which claims the benefit of U.S. Provisional Patent Application No. 63/042,602, filed on Jun. 23, 2020. These applications are hereby incorporated by reference herein.

TECHNICAL FIELD

The present disclosure pertains to imaging systems and methods for generating color Doppler images. In particular, imaging systems and methods for generating color Doppler images from short and undersampled radiofrequency (RF) ensembles.

BACKGROUND

Color Doppler (CD) has traditionally been used to diagnose atherosclerotic disease in the extracranial arteries and inspect the heart's hemodynamic properties. However, inspection of blood flows in the heart as well as in stenosed arteries often poses challenges due to high and turbulent blood velocities.

CD images are generated by estimating the mean phase shift within an ensemble of ultrasound pulses coming from the same sample volume (radiofrequency (RF)-ensemble). The most widely used phase shift estimation technique is the lag-1 autocorrelation operating on the slow-time RF-ensemble pulses. Power Doppler (PD) is extracted from the lag-0 auto-correlation. CD provides information relating to velocity (e.g., speed and direction) of blood flow. PD provides more sensitive detection of blood flow than CD, but does not provide directional information. Moving blood echoes can be separated from tissue background by applying a high-pass filter along the slow time direction (e.g., wall filter).

One determinant of CD signal quality is the number of pulses/slow-time observations in the ensemble (RF-ensemble size) used to generate a single CD image. A larger RF-ensemble size provides increased accuracy and sensitivity of CD blood flow velocity estimation compared to a smaller RF-ensemble size. Another CD quality factor is the pulse repetition frequency (PRF) of the ensemble pulses. The PRF determines the time-sampling rate of the Doppler signal and the highest blood flow velocity that can be recovered.

SUMMARY

As disclosed herein, artificial intelligence (e.g., deep learning) may be leveraged to correlate short/decimated ensembles with longer ensembles and/or ensembles with higher PRF in color Doppler images. In this manner, high quality color Doppler images may be generated from the short/decimated ensembles that mimic the appearance color Doppler images generated from longer ensembles and/or ensembles with higher PRF.

An ultrasound imaging system according to an example of the present disclosure may include a processor configured to receive ultrasound signals corresponding to a first radiofrequency (RF) ensemble comprising a first length, a first pulse repetition frequency (PRF), and a first sensitivity, estimate a second RF-ensemble from the first RF-ensemble based, at least in part, on reference ultrasound signals that correspond to at least one reference RF-ensemble comprising at least one of a second pulse repetition rate, a second length, or a second sensitivity different than the first RF-ensemble; and generate a color Doppler image using the second RF-ensemble A method according to an example of the present disclosure may include receiving ultrasound signals corresponding to a first radiofrequency (RF) ensemble comprising a first length, a first pulse repetition frequency (PRF), and a first sensitivity, estimating a second RF-ensemble from the first RF-ensemble based, at least in part, on reference ultrasound signals that correspond to at least one reference RF-ensemble comprising at least one of a second pulse repetition rate, a second length, or a second sensitivity different than the first RF-ensemble, and generating a color Doppler image using the second RF-ensemble.

In accordance with an example of the present disclosure, a non-transitory computer-readable medium may contain instructions, that when executed, may cause an imaging system to receive ultrasound signals corresponding to a first radiofrequency (RF) ensemble comprising a first length, a first pulse repetition frequency (PRF), and a first sensitivity, estimate a second RF-ensemble from the first RF-ensemble based, at least in part, on reference ultrasound signals that correspond to at least one reference RF-ensemble comprising at least one of a second pulse repetition rate, a second length, or a second sensitivity different than the first RF-ensemble, and generate a color Doppler image using the second RF-ensemble.

DETAILED DESCRIPTION

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Color Doppler (CD) images are generated by estimating the mean phase shift within an ensemble of ultrasound pulses coming from the same sample volume (radiofrequency (RF)-ensemble). In some examples, each pulse may correspond to a frame (e.g., RF frame). Long ensembles provide high quality CD images with sensitive and close estimations of blood flow velocity. However, long ensembles may lower frame rate, sometimes significantly, which may hinder diagnosis. Short ensemble lengths, which are commonly used in clinical scanners, extend the clutter bandwidth, making wall-filtering more challenging and decreasing sensitivity. Additionally, acquiring the mean Doppler shift from shorter RF-ensembles may lead to increased variability and thus decreased measurement accuracy.

Undersampled ensemble lengths (e.g., decimated ensembles) have increased sensitivity compared to the short ensembles. Undersampled ensembles may also provide greater opportunity for interleaved acquisitions (e.g., alternating ultrasound frames are acquired in different manners, such as Doppler and B-mode). However, undersampled ensembles may suffer from insufficient time-sampling of the Doppler signal. More specifically, when the detected Doppler frequency exceeds half the pulse repetition frequency (PRF) then the blood velocity can no longer be unambiguously recovered and aliasing may occur.

Figure 1:
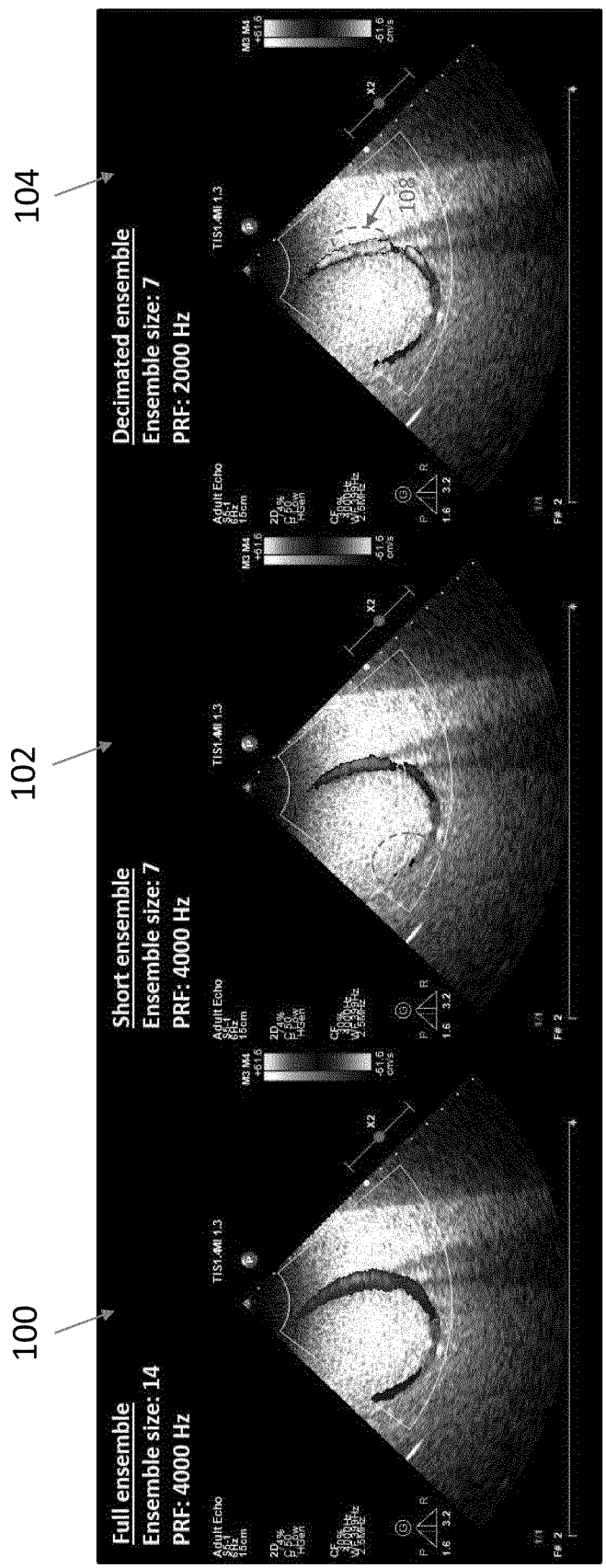
FIG. 1 shows example CD images for a long ensemble, a short, ensemble, and a decimated ensemble.

FIG. 1 shows example CD images 100, 102, and 104, for a long (or full) ensemble, a short ensemble, and a decimated ensemble, respectively. All of the CD images 100, 102, 104, were acquired from a flow phantom. The long ensemble CD image 100 was generated from an ensemble including fourteen ultrasound pulses at a pulse repetition frequency (PRF) of 4,000 Hz. The short ensemble CD image 102 was generated from an ensemble including seven ultrasound pulses at a PRF of 4,000 Hz. As noted above, the short ensemble has reduced sensitivity compared to the long ensemble. For example, in region 106, the CD image 102 fails to detect all of the flow that was detected in CD image 100. The decimated ensemble CD image 104 was generated from an ensemble including seven ultrasound pulses at a PRF of 2,000 Hz. While the CD image 104 shows greater sensitivity to flow than CD image 102, aliasing of velocity values can be observed, for example, in region 108.

Consequently, it may be desirable to gain the advantages of long ensembles with high PRF (e.g., high CD image quality as shown in CD image 100) while retaining the flexibility of short/undersampled ensembles (e.g., higher imaging frame rate, interleaving capabilities).

As disclosed herein, artificial intelligence (e.g., deep learning) may be leveraged to link short/undersampled ensembles to CD images generated using longer ensembles and/or ensembles with higher PRF. More specifically, a deep learning framework including one or more convolutional neural networks (CNN) with short/decimated ensembles as input data and long and/or high PRF ensemble CD images as output data. Once trained, the deep learning framework may provide CD images from short/undersampled ensembles that are higher quality (e.g., higher sensitivity, more accurate velocity estimations) compared to typical CD images generated from short/undersampled ensembles. In other words, the CD images provided by the deep learning framework may provide CD images closer to the quality of CD images generated from long and/or high PRF ensembles.

Figure 2:
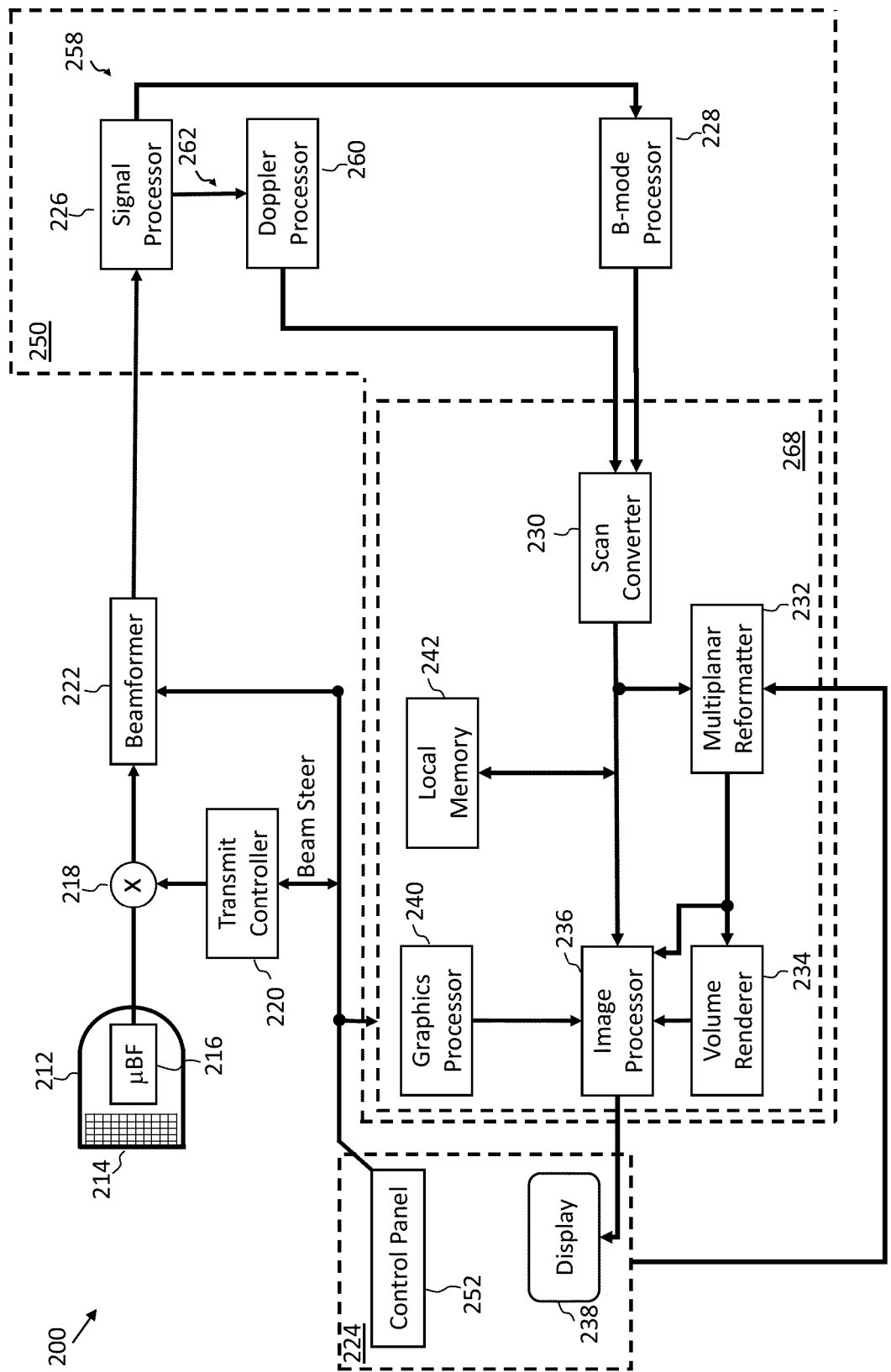
FIG. 2 is a block diagram of an ultrasound system in accordance with principles of the present disclosure.

FIG. 2 shows a block diagram of an ultrasound imaging system 200 constructed in accordance with the principles of the present disclosure. An ultrasound imaging system 200 according to the present disclosure may include a transducer array 214, which may be included in an ultrasound probe 212, for example an external probe or an internal probe such as an Intra Cardiac Echography (ICE) probe or a Trans Esophagus Echography (TEE) probe. In other embodiments, the transducer array 214 may be in the form of a flexible array configured to be conformably applied to a surface of subject to be imaged (e.g., patient). The transducer array 214 is configured to transmit ultrasound signals (e.g., beams, waves) and receive echoes responsive to the ultrasound signals. A variety of transducer arrays may be used, e.g., linear arrays, curved arrays, or phased arrays. The transducer array 214, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction.

In some embodiments, the transducer array 214 may be coupled to a microbeamformer 116, which may be located in the ultrasound probe 212, and which may control the transmission and reception of signals by the transducer elements in the array 214. In some embodiments, the microbeamformer 216 may control the transmission and reception of signals by active elements in the array 214 (e.g., an active subset of elements of the array that define the active aperture at any given time).

In some embodiments, the microbeamformer 216 may be coupled, e.g., by a probe cable or wirelessly, to a transmit/receive (T/R) switch 218, which switches between transmission and reception and protects the main beamformer 222 from high energy transmit signals. In some embodiments, for example in portable ultrasound systems, the T/R switch 218 and other elements in the system can be included in the ultrasound probe 212 rather than in the ultrasound system base, which may house the image processing electronics. An ultrasound system base typically includes software and hardware components including circuitry for signal processing and image data generation as well as executable instructions for providing a user interface (e.g., processing circuitry 250 and user interface 224).

The transmission of ultrasonic signals from the transducer array 214 under control of the microbeamformer 216 is directed by the transmit controller 220, which may be coupled to the T/R switch 218 and a main beamformer 222. The transmit controller 220 may control the direction in which beams are steered. Beams may be steered straight ahead from (orthogonal to) the transducer array 214, or at different angles for a wider field of view. The transmit controller 220 may also be coupled to a user interface 224 and receive input from the user's operation of a user control. The user interface 224 may include one or more input devices such as a control panel 252, which may include one or more mechanical controls (e.g., buttons, encoders, etc.), touch sensitive controls (e.g., a trackpad, a touchscreen, or the like), and/or other known input devices.

In some embodiments, the partially beamformed signals produced by the microbeamformer 216 may be coupled to a main beamformer 222 where partially beamformed signals from individual patches of transducer elements may be combined into a fully beamformed signal. In some embodiments, microbeamformer 216 is omitted, and the transducer array 214 is under the control of the main beamformer 222 which performs all beamforming of signals. In embodiments with and without the microbeamformer 216, the beamformed signals of the main beamformer 222 are coupled to processing circuitry 250, which may include one or more processors (e.g., a signal processor 226, a B-mode processor 228, a Doppler processor 260, and one or more image generation and processing components 268) configured to produce an ultrasound image from the beamformed signals (e.g., beamformed RF data).

The signal processor 226 may be configured to process the received beamformed RF data in various ways, such as bandpass filtering, decimation, I and Q component separation, and harmonic signal separation. The signal processor 226 may also perform additional signal enhancement such as speckle reduction, signal compounding, and noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data). For example, the system may include a B-mode signal path 258 which couples the signals from the signal processor 226 to a B-mode processor 228 for producing B-mode image data.

The B-mode processor can employ amplitude detection for the imaging of structures in the body. The signals produced by the B-mode processor 228 may be coupled to a scan converter 230 and/or a multiplanar reformatter 232. The scan converter 230 may be configured to arrange the echo signals from the spatial relationship in which they were received to a desired image format. For instance, the scan converter 230 may arrange the echo signal into a two dimensional (2D) sector-shaped format, or a pyramidal or otherwise shaped three dimensional (3D) format. The multiplanar reformatter 232 can convert echoes which are received from points in a common plane in a volumetric region of the body into an ultrasonic image (e.g., a B-mode image) of that plane, for example as described in U.S. Pat. No. 6,443,896 (Detmer). The scan converter 230 and multiplanar reformatter 232 may be implemented as one or more processors in some embodiments.

A volume renderer 234 may generate an image (also referred to as a projection, render, or rendering) of the 3D dataset as viewed from a given reference point, e.g., as described in U.S. Pat. No. 6,530,885 (Entrekin et al.). The volume renderer 234 may be implemented as one or more processors in some embodiments. The volume renderer 234 may generate a render, such as a positive render or a negative render, by any known or future known technique such as surface rendering and maximum intensity rendering.

In some embodiments, the system may include a Doppler signal path 262 which couples the output from the signal processor 226 to a Doppler processor 260. The Doppler processor 260 may be configured to estimate the Doppler shift and generate Doppler image data. The Doppler image data may include color data which is then overlaid with B-mode (i.e. grayscale) image data for display. The Doppler processor 260 may be configured to filter out unwanted signals (i.e., noise or clutter associated with non-moving tissue), for example using a wall filter. The Doppler processor 260 may be further configured to estimate velocity and power in accordance with known techniques. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some embodiments, the velocity and/or power estimates may undergo further threshold detection to further reduce noise, as well as segmentation and post-processing such as filling and smoothing. The velocity and/or power estimates may then be mapped to a desired range of display colors in accordance with a color map. The color data, also referred to as Doppler image data, may then be coupled to the scan converter 230, where the Doppler image data may be converted to the desired image format and overlaid on the B-mode image of the tissue structure to form a color Doppler or a power Doppler image. In some examples, the power estimates (e.g., the lag-0 autocorrelation information) may be used to mask or segment flow in the color Doppler (e.g., velocity estimates) before overlaying the color Doppler image onto the B-mode image.

According to embodiments of the present disclosure, the ultrasound probe 212 may transmit an ensemble of ultrasound pulses (e.g., RF-ensemble or simply ensemble). The ensemble may be a short and/or undersampled ensemble in some embodiments. The ultrasound probe 212 may receive ultrasound signals responsive to the transmitted ensemble. These signals may be provided to the Doppler processor 260 via the beamformer 222 and signal processor 226. The Doppler processor 260 may generate an enhanced CD image based on the received signals. In some embodiments, the enhanced CD image generated by the Doppler processor 260 based on the signals from short and/or undersampled ensemble may have a higher sensitivity to flow and/or more accurate velocity estimates (e.g., reduced aliasing) compared to typical CD images generated from short and/or undersampled ensemble. In some examples, the enhanced CD image generated by Doppler processor 260 may have sensitivity and accuracy closer or equal to CD images generated by long and/or high PRF ensembles. In some examples, the signals used to generate the enhanced CD image may be wall-filtered. In other examples, the signals used to generate the enhanced CD image may not undergo wall filtering.

In some embodiments, the Doppler processor 260 may be implemented by one or more processors and/or application specific integrated circuits. In some embodiments, the Doppler processor 260 may include any one or more machine learning, artificial intelligence algorithms, and/or multiple neural networks. In some examples, Doppler processor 260 may include a deep neural network (DNN), a convolutional neural network (CNN), a recurrent neural network (RNN), an autoencoder neural network, or the like, to generate the enhanced CD image from short and/or undersampled ensembles. The neural network may be implemented in hardware (e.g., neurons are represented by physical components) and/or software (e.g., neurons and pathways implemented in a software application) components. The neural network implemented according to the present disclosure may use a variety of topologies and learning algorithms for training the neural network to produce the desired output. For example, a software-based neural network may be implemented using a processor (e.g., single or multi-core CPU, a single GPU or GPU cluster, or multiple processors arranged for parallel-processing) configured to execute instructions, which may be stored in computer readable medium, and which when executed cause the processor to perform a trained algorithm for generating the enhanced CD image from short and/or undersampled ensembles. In some embodiments, the Doppler processor 260 may implement a neural network in combination with other image processing methods (e.g., segmentation, histogram analysis).

In various embodiments, the neural network(s) may be trained using any of a variety of currently known or later developed learning techniques to obtain a neural network (e.g., a trained algorithm or hardware-based system of nodes) that is configured to analyze input data in the form of ultrasound images, measurements, and/or statistics. In some embodiments, the neural network may be statically trained. That is, the neural network may be trained with a data set and deployed on the Doppler processor 260. In some embodiments, the neural network may be dynamically trained. In these embodiments, the neural network may be trained with an initial data set and deployed on the Doppler processor 260. However, the neural network may continue to train and be modified based on ultrasound images acquired by the system 200 after deployment of the neural network on the Doppler processor 260.

Outputs from the scan converter 230, the multiplanar reformatter 232, and/or the volume renderer 234 may be coupled to an image processor 236 for further enhancement, buffering and temporary storage before being displayed on an image display 238. A graphics processor 240 may generate graphic overlays for display with the images. These graphic overlays can contain, e.g., standard identifying information such as patient name, date and time of the image, imaging parameters, and the like. For these purposes the graphics processor may be configured to receive input from the user interface 224, such as a typed patient name or other annotations. The user interface 224 can also be coupled to the multiplanar reformatter 232 for selection and control of a display of multiple multiplanar reformatted (MPR) images.

The system 200 may include local memory 242. Local memory 242 may be implemented as any suitable non-transitory computer readable medium (e.g., flash drive, disk drive). Local memory 242 may store data generated by the system 200 including ultrasound images, executable instructions, imaging parameters, training data sets, or any other information necessary for the operation of the system 200.

As mentioned previously system 200 includes user interface 224. User interface 224 may include display 238 and control panel 252. The display 238 may include a display device implemented using a variety of known display technologies, such as LCD, LED, OLED, or plasma display technology. In some embodiments, display 238 may comprise multiple displays. The control panel 252 may be configured to receive user inputs (e.g., ensemble length, imaging mode). The control panel 252 may include one or more hard controls (e.g., buttons, knobs, dials, encoders, mouse, trackball or others). In some embodiments, the control panel 252 may additionally or alternatively include soft controls (e.g., GUI control elements or simply, GUI controls) provided on a touch sensitive display. In some embodiments, display 238 may be a touch sensitive display that includes one or more soft controls of the control panel 252.

In some embodiments, various components shown in FIG. 2 may be combined. For instance, image processor 236 and graphics processor 240 may be implemented as a single processor. In some embodiments, various components shown in FIG. 2 may be implemented as separate components. For example, signal processor 226 may be implemented as separate signal processors for each imaging mode (e.g., B-mode, Doppler). In some embodiments, one or more of the various processors shown in FIG. 2 may be implemented by general purpose processors and/or microprocessors configured to perform the specified tasks. In some embodiments, one or more of the various processors may be implemented as application specific circuits. In some embodiments, one or more of the various processors (e.g., image processor 236) may be implemented with one or more graphical processing units (GPU).

Figure 3:
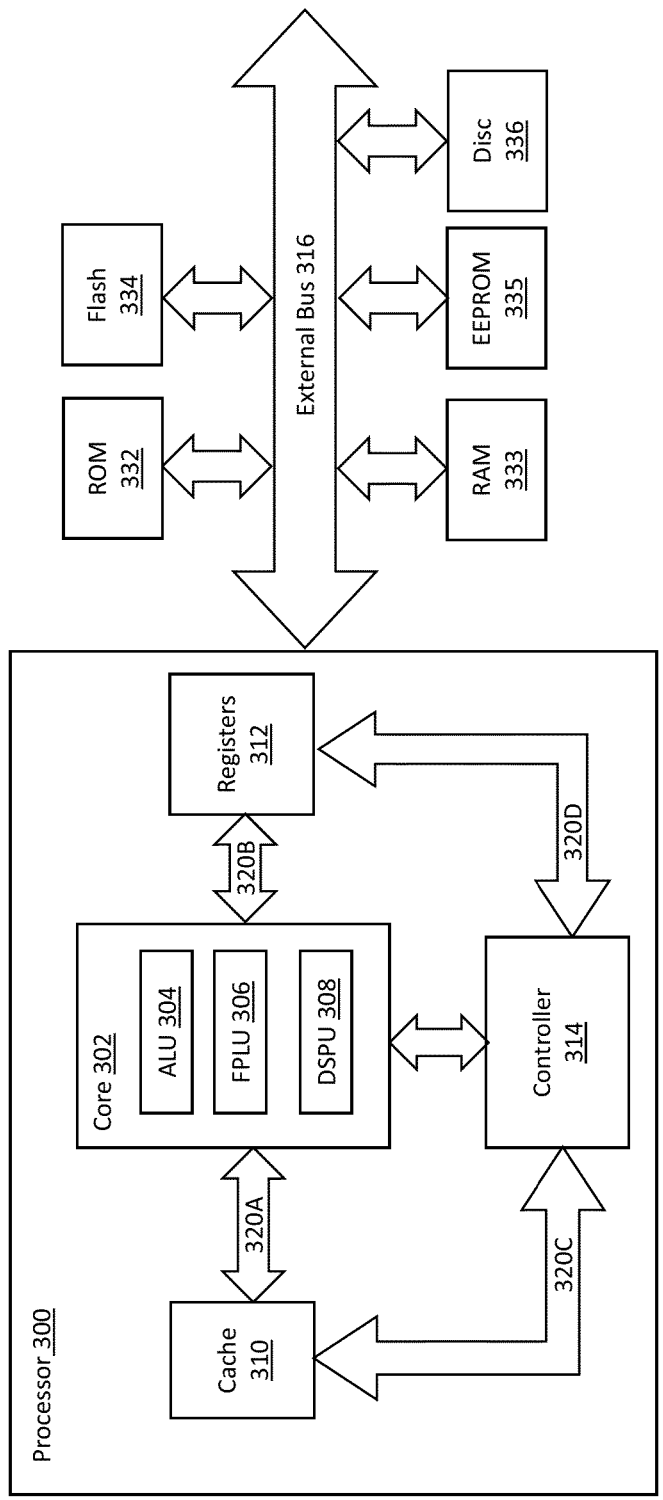
FIG. 3 is a block diagram illustrating an example processor in accordance with principles of the present disclosure.

FIG. 3 is a block diagram illustrating an example processor 300 according to principles of the present disclosure. Processor 300 may be used to implement one or more processors and/or controllers described herein, for example, image processor 236 shown in FIG. 2 and/or any other processor or controller shown in FIG. 2. Processor 300 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 300 may include one or more cores 302. The core 302 may include one or more arithmetic logic units (ALU) 304. In some embodiments, the core 302 may include a floating point logic unit (FPLU) 306 and/or a digital signal processing unit (DSPU) 308 in addition to or instead of the ALU 304.

The processor 300 may include one or more registers 312 communicatively coupled to the core 302. The registers 312 may be implemented using dedicated logic gate circuits (e.g., flip-flops) and/or any memory technology. In some embodiments the registers 312 may be implemented using static memory. The register may provide data, instructions and addresses to the core 302.

In some embodiments, processor 300 may include one or more levels of cache memory 310 communicatively coupled to the core 302. The cache memory 310 may provide computer-readable instructions to the core 302 for execution. The cache memory 310 may provide data for processing by the core 302. In some embodiments, the computer-readable instructions may have been provided to the cache memory 310 by a local memory, for example, local memory attached to the external bus 316. The cache memory 310 may be implemented with any suitable cache memory type, for example, metal-oxide semiconductor (MOS) memory such as static random access memory (SRAM), dynamic random access memory (DRAM), and/or any other suitable memory technology.

The processor 300 may include a controller 314, which may control input to the processor 300 from other processors and/or components included in a system (e.g., control panel 252 and scan converter 230 shown in FIG. 2) and/or outputs from the processor 300 to other processors and/or components included in the system (e.g., display 238 and volume renderer 234 shown in FIG. 2). Controller 314 may control the data paths in the ALU 304, FPLU 306 and/or DSPU 308. Controller 314 may be implemented as one or more state machines, data paths and/or dedicated control logic. The gates of controller 314 may be implemented as standalone gates, FPGA, ASIC or any other suitable technology.

The registers 312 and the cache memory 310 may communicate with controller 314 and core 302 via internal connections 320A, 320B, 320C and 320D. Internal connections may implemented as a bus, multiplexor, crossbar switch, and/or any other suitable connection technology.

Inputs and outputs for the processor 300 may be provided via a bus 316, which may include one or more conductive lines. The bus 316 may be communicatively coupled to one or more components of processor 300, for example the controller 314, cache 310, and/or register 312. The bus 316 may be coupled to one or more components of the system, such as display 238 and control panel 252 mentioned previously.

The bus 316 may be coupled to one or more external memories. The external memories may include Read Only Memory (ROM) 332. ROM 332 may be a masked ROM, Electronically Programmable Read Only Memory (EPROM) or any other suitable technology. The external memory may include Random Access Memory (RAM) 333. RAM 333 may be a static RAM, battery backed up static RAM, Dynamic RAM (DRAM) or any other suitable technology. The external memory may include Electrically Erasable Programmable Read Only Memory (EEPROM) 335. The external memory may include Flash memory 334. The external memory may include a magnetic storage device such as disc 336. In some embodiments, the external memories may be included in a system, such as ultrasound imaging system 200 shown in FIG. 2, for example local memory 242.

Figure 4:
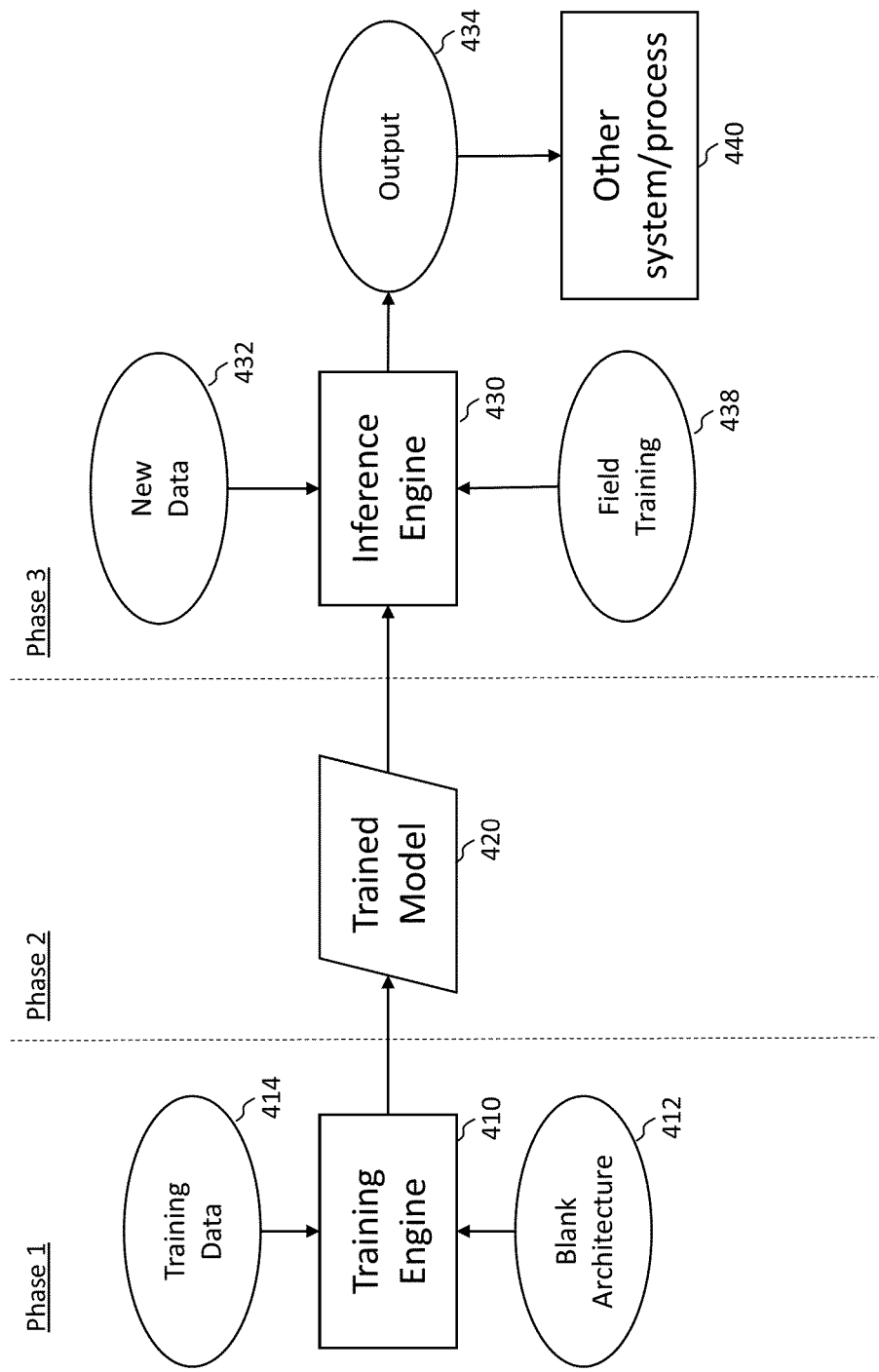
FIG. 4 is a block diagram of a process for training and deployment of a neural network in accordance with the principles of the present disclosure.

FIG. 4 shows a block diagram of a process for training and deployment of a neural network in accordance with the principles of the present disclosure. The process shown in FIG. 4 may be used to train a neural network included in the Doppler processor 260. The left hand side of FIG. 4, phase 1, illustrates the training of a neural network. To train the neural network, training sets which include multiple instances of input arrays and output classifications may be presented to the training algorithm(s) of the neural network(s) (e.g., AlexNet training algorithm, as described by Krizhevsky, A., Sutskever, I. and Hinton, G. E. "*ImageNet Classification with Deep Convolutional Neural Networks*," NIPS 2012 or its descendants). Training may involve the selection of a starting network architecture 412 and the preparation of training data 414. The starting network architecture 412 may be a blank architecture (e.g., an architecture with defined layers and arrangement of nodes but without any previously trained weights) or a partially trained network, such as the inception networks, which may then be further tailored for classification of ultrasound images. The starting architecture 412 (e.g., blank weights) and training data 414 are provided to a training engine 410 (e.g., ADAM optimizer) for training the model. Upon sufficient number of iterations (e.g., when the model performs consistently within an acceptable error), the model 420 is said to be trained and ready for deployment, which is illustrated in the middle of FIG. 4, phase 2. The right hand side of FIG. 4, or phase 3, the trained model 420 is applied (via inference engine 430) for analysis of new data 432, which is data that has not been presented to the model during the initial training (in phase 1). For example, the new data 432 may include unknown images such as live ultrasound images acquired during a scan of a patient (e.g., cardiac images during an echocardiography exam). The trained model 420 implemented via engine 430 is used to classify the unknown images in accordance with the training of the model 420 to provide an output 434 (e.g., generating an enhanced CD image from short and/or undersampled ensembles). The output 434 may then be used by the system for subsequent processes 440 (e.g., displaying the enhanced CD image, performing additional image processing on the enhanced CD image).

In the embodiments where the trained model 420 is used to implement a neural network of the Doppler processor 260, the starting architecture may be that of a convolutional neural network, or a deep convolutional neural network, which may be trained to generate the enhanced CD image from short and/or undersampled ensembles. The training data 414 may include multiple (hundreds, often thousands or even more) annotated/labeled images, also referred to as training images. It will be understood that the training image need not include a full image produced by an imagining system (e.g., representative of the full field of view of an ultrasound probe or entire MM volume) but may include patches or portions of images, for example, those portions that include flow.

In various embodiments, the trained neural network may be implemented, at least in part, in a computer-readable medium comprising executable instructions executed by a processor, e.g., Doppler processor 260.

Figure 5:
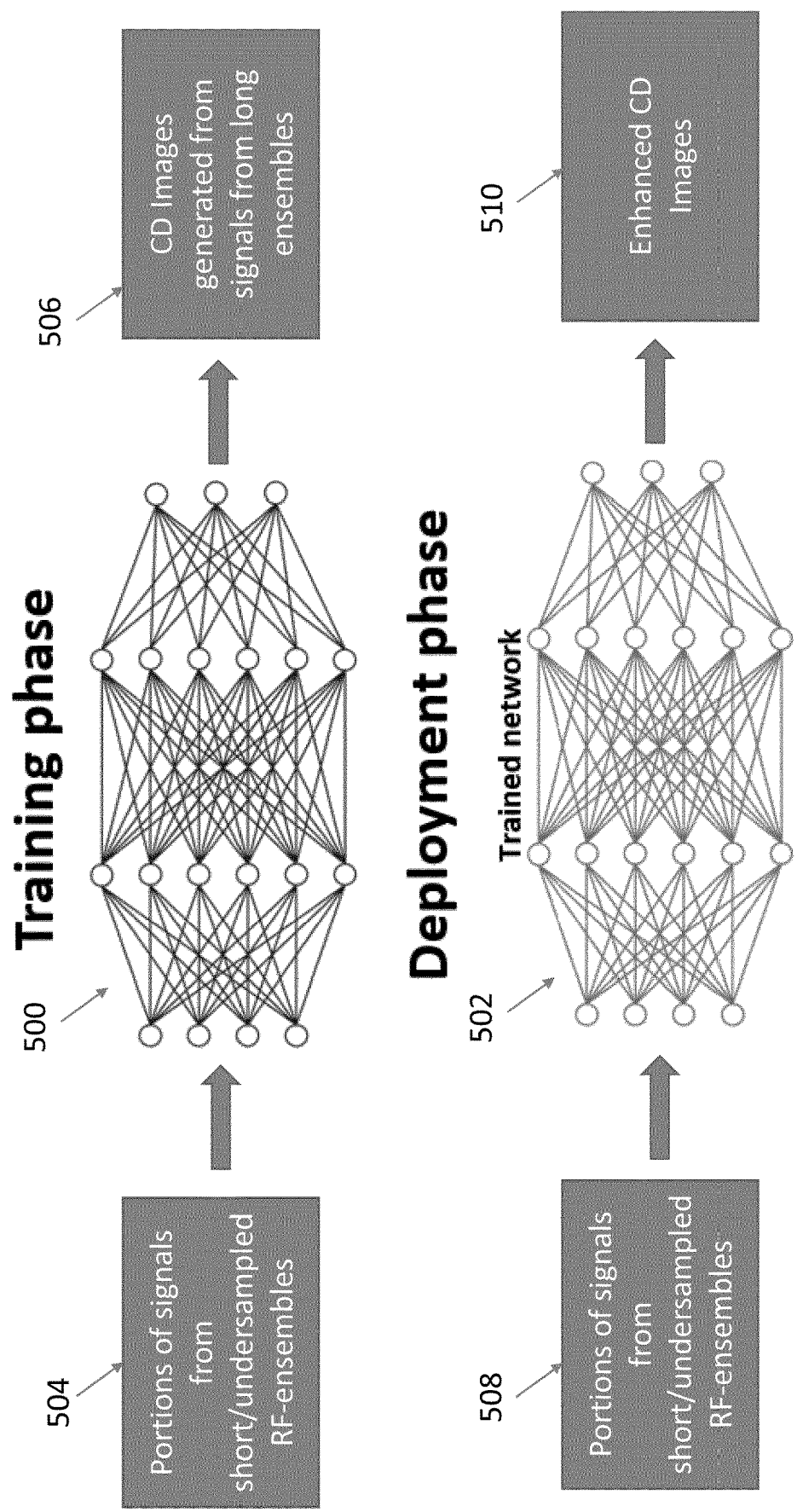
FIG. 5 shows an overview of a training phase and a deployment phase of a neural network in accordance with the principles of the present disclosure.

FIG. 5 shows an overview of a training phase and a deployment phase of a neural network in accordance with the principles of the present disclosure. During the training phase, the untrained neural network 500 receives a training set including portions of signals and/or whole image signals from short and/or undersampled RF-ensembles as inputs 504. In some examples, the signals may be wall-filtered. In other examples, the signals may not be wall-filtered. The portions of the signals may be portions that include flow (e.g., blood flow in a vessel). In some examples, all of the signals from the short and/or undersampled RF-ensembles may be provided as inputs (e.g., blood flow in a vessel and signals from surrounding tissue). However, this may train the neural network 500 on noise, which may lead to the generation of artifacts in the outputs (e.g., false indications of flow in unmoving tissue). The training set may further include a desired set of outputs 506 associated with each of the inputs 504. The outputs 506 may include CD images generated based on signals from long and/or high PRF ensembles. In some examples, the outputs 506 may include components of CD images such as the phase of the lag-1 autocorrelation or the log compressed lag-0 autocorrelation. As discussed in reference to FIG. 4, the untrained neural network 500 may adapt itself (e.g., adjust weights, a number of layers, a number of nodes in each layer, etc.) until the neural network 500 can reliably generate an output identical or sufficiently similar to the desired output 506 based on the corresponding input 504.

After the training phase, the trained neural network 502 may be deployed (e.g., in an ultrasound imaging system, such as ultrasound imaging system 200). The trained neural network 502 may receive previously unseen (e.g., new) portions of signals from short/undersampled RF-ensembles as inputs 508. In some examples, the entirety of the signals may be provided to the trained neural network 502. The signals may or may not be wall-filtered. The signals may have been acquired by an ultrasound probe, such as ultrasound probe 212. The trained neural network 502 may perform operations on (e.g., process) the inputs 508 to generate enhanced CD images as outputs 510. As discussed previously, the enhanced CD images may more closely resemble CD images generated from long and/or high PRF ensembles than CD images generated from the short/undersampled RF-ensembles without use of the trained neural network 502.

Figure 6:
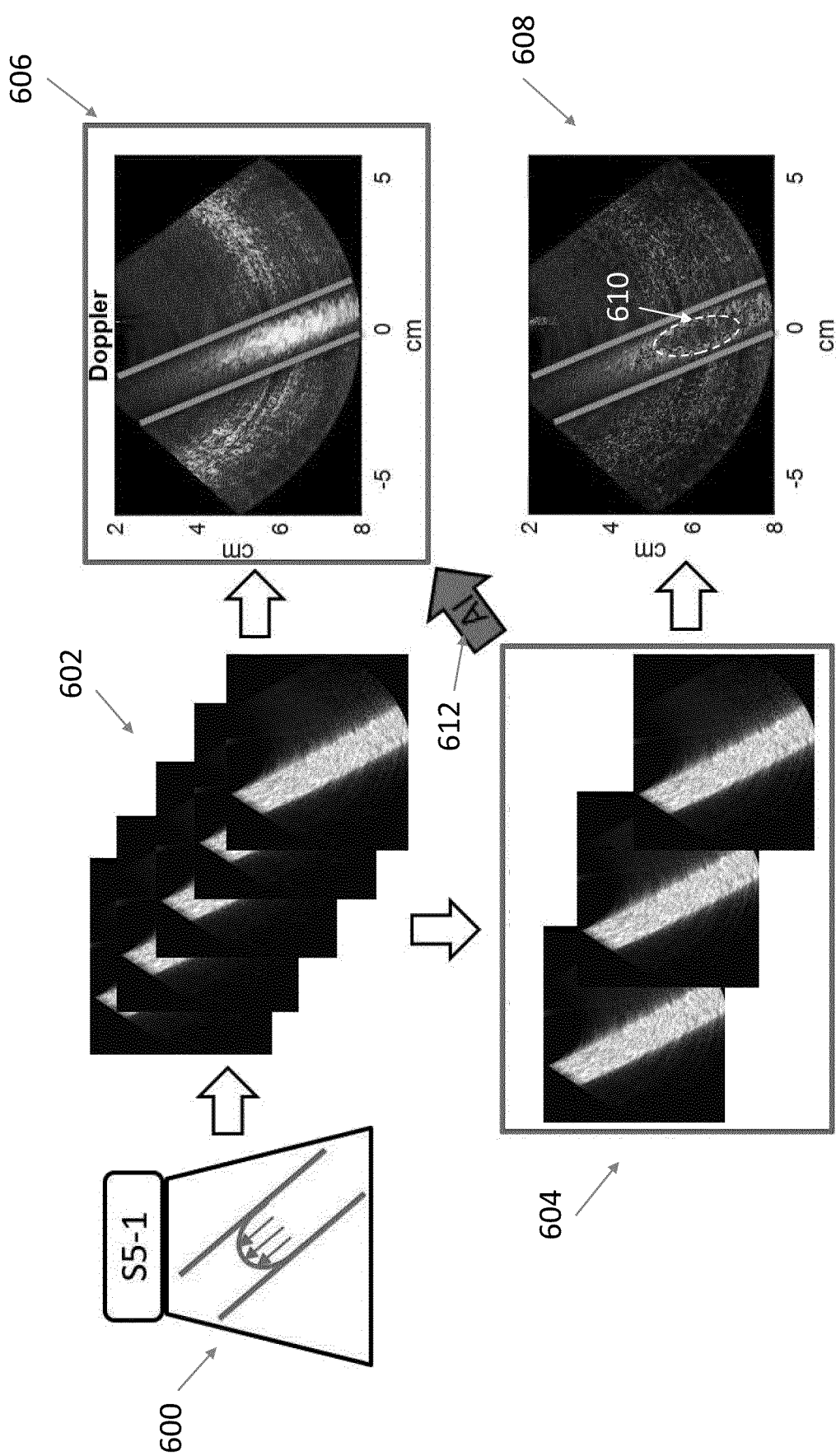
FIG. 6 illustrates an example workflow for generating a training data set in accordance with the principles of the present disclosure.

FIG. 6 illustrates an example process or workflow for generating a training data set in accordance with the principles of the present disclosure. In a first step 600, signals from a long and/or high PRF RF-ensemble may be acquired. The signals may be in vivo signals of one or more blood vessels, a heart or portions thereof, or other region with flow acquired by an ultrasound probe. In some examples, the signals may be acquired by an ultrasound probe from a flow phantom (e.g., a Gammex flow phantom by Sun Nuclear Corporation). In some examples, the signals may be acquired by being simulated using ultrasound simulation software (e.g., Field II developed by Jørgen Arendt Jensen at the Technical University of Denmark). The signals acquired at step 600 may correspond to multiple frames as shown at step 602. For example, a long ensemble may generate 10-20 frames in some applications. A subset of the frames from the long and/or high PRF ensemble at step 602 may be used to provide a set of frames corresponding to a short and/or undersampled ensemble at step 604.

The frames from the long and/or high PRF ensemble may be used to generate a CD image at step 606. The CD image generated at step 606 may be a high quality CD image (e.g., high sensitivity and accurate velocity estimates). The frames from the short and/or undersampled ensemble may also be used to generate a CD image at step 608. However, step 608 is not required to generate the training data set and is provided only to illustrate the difference in quality between the CD image generated from the long and/or high PRF ensemble at step 606 and the CD image generated from the short ensemble. For example, in the image at step 608 in the region 610, aliasing of velocity values can be observed.

Finally, at step 612, the short and/or undersampled ensembles generated at step 604 are linked to corresponding CD images generated from the long and/or high PRF ensembles at step 606. These input-output pairs are then provided to a neural network (e.g., neural network 500) for training.

Two examples for generating training data are provided herein. However, these examples are provided only for explanatory purposes and the disclosure is not limited to the examples disclosed herein for generating training data.

In a first example according to the present disclosure, simulation data was used to train a CNN. Flow phantoms were generated by simulating scatterers within boundaries of an assumed vessel (e.g., 18 simulated vessels, vessel radius=1.5-7.5 mm). Scatterer motion was simulated according to a parabolic flow profile. The angle and the radius of the assumed vessel as well as the peak flow velocities along it were randomly varied for each phantom.

Doppler imaging of the simulated flow phantoms was simulated using Field II. An S5-1 transducer was simulated (center frequency 2.5 MHz, 50% bandwidth) and an ensemble of 2N RF-frames was generated for each of the phantoms at an assumed PRF (e.g., 2N=10, PRF=2000 Hz). The per channel RF-signals were then sampled, beamformed and QBP filtered.

Thus, 3-D datasets were obtained with dimensions: samples×receive lines×ensemble size. The RF-ensembles were then decimated by a factor of 2 (CNN input, e.g. N=5, PRF=1000 Hz). A 1-D auto-correlation method was employed to estimate the Doppler phase shift for the original RF-ensembles (CNN target). Patches were extracted from each pair of training inputs/targets (e.g. 800 patches sized 100 samples×20 receive lines (×5 RF-frames for RF ensembles)). Wall filtering was not applied in the simulation datasets since only flow was simulated (e.g., no tissue scatterers were simulated), essentially imitating ideally wall-filtered datasets.

In a second example according to the present disclosure, a Gammex flow phantom was scanned with an EPIQ ultrasound scanner (available from Philips Healthcare) to generate training data for the CNN. The flow phantom velocities varied for each acquisition. An S5-1 transducer was used (center frequency 2.5 MHz, 50% bandwidth) and ensembles of 14 pulses at a specific PRF were obtained and QBP-filtered (long ensemble, Nle=14, PRF=4000 Hz). In this example, only the 4 first pulses of the long ensemble were extracted to be used as the CNN input for the short ensemble (Nse=4 pulses, PRF=4000 Hz). The long and short ensembles were wall-filtered with appropriate wall filters for each case (e.g., high-pass filter). Wall filtering resulted to dropping out a small number (N1) of RF-ensemble frames (e.g. Nle'=Nle−N1=12, Nse'=Nse−N1=2).

A 1-D auto-correlation method was employed to estimate the mean Doppler phase shift of the long RF-ensemble (e.g., desired output of the CNN). Patches were extracted from each pair of training inputs/desired outputs (e.g., 500 patches sized 200 samples×20 receive lines (×2 RF-frames for RF ensembles)). A Doppler-specific augmentation used to facilitate training was used and involved selecting training patches only around points where the power of the Doppler signal (zero-lag autocorrelation of the RF-ensemble) exceeded a user-defined and depth-dependent threshold. This reduced training the CNN on noise.

Each of the RF-ensemble patches was zero-centered and normalized to unit power. The normalized RF-ensemble patches and the corresponding CD phase image patches were shuffled in order to facilitate generalization and split into training and validation datasets.

Figure 7:
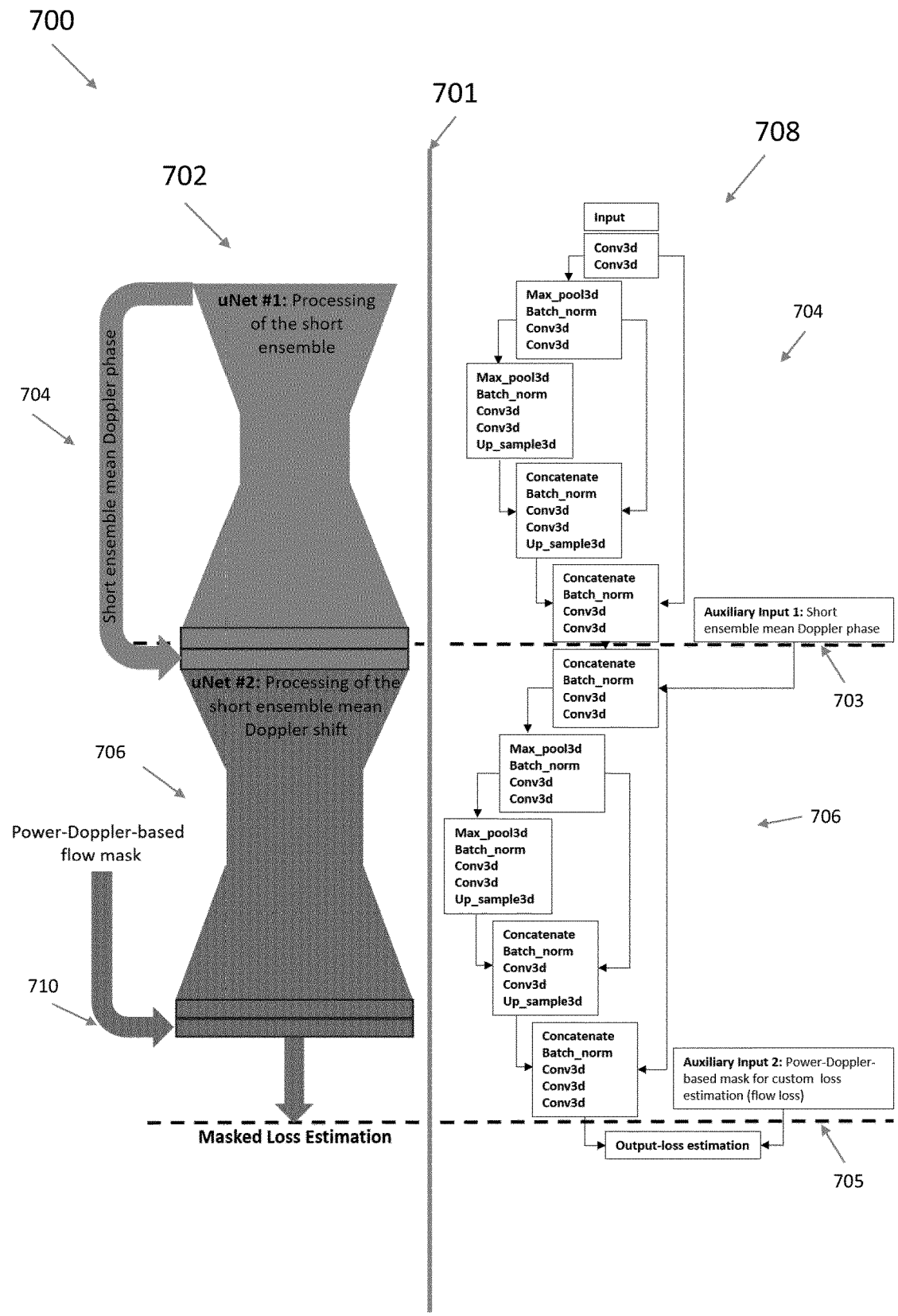
FIG. 7 is a diagram of a neural network in accordance with the principles of the present disclosure.

FIG. 7 is a diagram of one example of a neural network in accordance with the principles of the present disclosure. The neural network 700 is a convolutional neural network with two serial uNets. On the left-hand side of line 701, a schematic 702 of the neural network 700 is shown, illustrating the first uNet 704 and second uNet 706. On the right-hand side of line 701 is a block diagram 708 of the corresponding architecture of the neural network 700. Horizontal dashed lines 703 and 705 provide indications as to which portions of the block diagram 708 correspond with which uNet 704, 706 in the schematic 702.

In the example shown in FIG. 7, the first uNet 704 focuses on extracting information from each individual frame of the short and/or undersampled RF ensemble while keeping the ensemble dimension the same. Subsequently, a convolutional layer compresses the processed short and/or undersampled RF ensemble into a single mean Doppler phase image. The result of this layer is concatenated with the short and/or undersampled ensemble mean Doppler phase (Auxiliary Input #1) which may facilitate mean Doppler phase estimation (e.g., use features of the short R1 phase). This result is then fed into the second uNet 706, which focuses on processing the estimated mean Doppler phase to match the estimated mean Doppler phase to the long and/or high PRF ensemble estimated Doppler phase to generate the enhanced CD image. In other words, the first uNet 704 receives the short and/or undersampled RF ensemble and outputs a mean Doppler phase image and a short and/or undersampled ensemble Doppler phase. The second uNet 706 receives the outputs of the first uNet as inputs and outputs the enhanced CD image. In some examples, the second uNet 706 may output a generated RF-ensemble from which to generate the enhanced CD image.

Optionally, in some examples, such as the one shown in FIG. 7, a Doppler-specific augmentation of the neural network 700 may be included during the training phase. The Doppler-specific augmentation may include a custom masked mean squared error (MSE) loss. More specifically, after high-pass wall-filtering non-flow regions may exhibit high-magnitude, noisy Doppler shift values that may dominate the MSE used during training, thus biasing it and causing artifacts to appear in the predicted images. To minimize this issue, a mask based on long-ensemble power Doppler may be implemented. Long-ensemble power Doppler images may be thresholded according to a depth-dependent threshold and then convolved with a Gaussian kernel to obtain a smooth mask of the Doppler flow. The mask may be concatenated with the CNN's output during training and used to estimate a custom weighted MSE loss function as indicated by arrow 710 and the box labelled "Auxiliary Input 2". Using the masked loss function during training focuses the neural network 700 on flow regions and prevents or reduces biases due to high background values. During testing this last concatenation layer may be pruned, as no error metric is computed Optionally, in some examples, an adversarial loss may be used during training. The adversarial loss may give the resulting enhanced CD images a more natural look. The adversarial loss may be added by using conditional generative adversarial networks (cGAN) or a similar model (collectively, a discriminator network). In these examples, a discriminator network may be trained simultaneously with the neural network 700 to distinguish the enhanced CD images from the CD images generated from long and/or high PRF ensembles based on a binary cross-entropy loss, which is provided by:

$$\text{Binary\_cross\_entropy} = -\Sigma(\text{label}_i \cdot \log(p(\text{label}_i)) + (1-\text{label}_i) \cdot \log(1-p(\text{label}_i))) \quad \text{Equation 1}$$

Where p is a probability function and $\text{label}_i$ is the label for the i-th input frame into the adversarial network. For example, if an input frame is an enhanced CD image generated by the neural network 700 (e.g., "fake"), the $\text{label}_i$ may =1 and if the input frame is a CD image generated from a long and/or high PRF RF-ensemble (e.g., "real"), the $\text{label}_i$ may =0. At the output of the discriminator network, a probability is computed that the input i-th frame is "fake." Thus, $p(\text{label}_i)$ may have a value between 0 and 1, inclusive. The binary cross-entropy loss is minimized when $p(\text{label}_i)$ corresponds to the correct label (e.g., when $\text{label}_i=1 \rightarrow p(\text{label}_i)=1$ and $\text{label}_i=0 \rightarrow p(\text{label}_i)=0$). The binary cross-entropy loss is maximized when the $p(\text{label}_i)$ is incorrect (e.g., $\text{label}_i=0 \rightarrow p(\text{label}_i)=1$ and $\text{label}_i=1 \rightarrow p(\text{label}_i)=0$).

The discriminator network is trained to differentiate the output of the neural network 700 (e.g., differentiate between the enhanced CD images and the CD images from long and/or high PRF RF-ensembles) to minimize the loss in Equation 1. Once the discriminator network has been trained to minimize the loss, the discriminator network is frozen and the neural network 700 continues to train to minimize the total loss. In some examples, the total adversarial loss used to train the neural network 700 may be determined by the mean of the weighted MSE and the binary cross-entropy losses.

The use of the MSE loss and/or adversarial loss to modify the neural network 700 may give the background noise higher values that are closer to the ones expected with regular Doppler processing. This may facilitate processing of images as no changes in the signal and image processing (SIP) of the ultrasound system (e.g., signal processor 226, image processor 236) and/or filtering out of the background noise may be required.

The neural network 700 shown in FIG. 7 is provided only as an example. Other neural networks may be used, for example, conventional serial CNNs.

Figure 8:
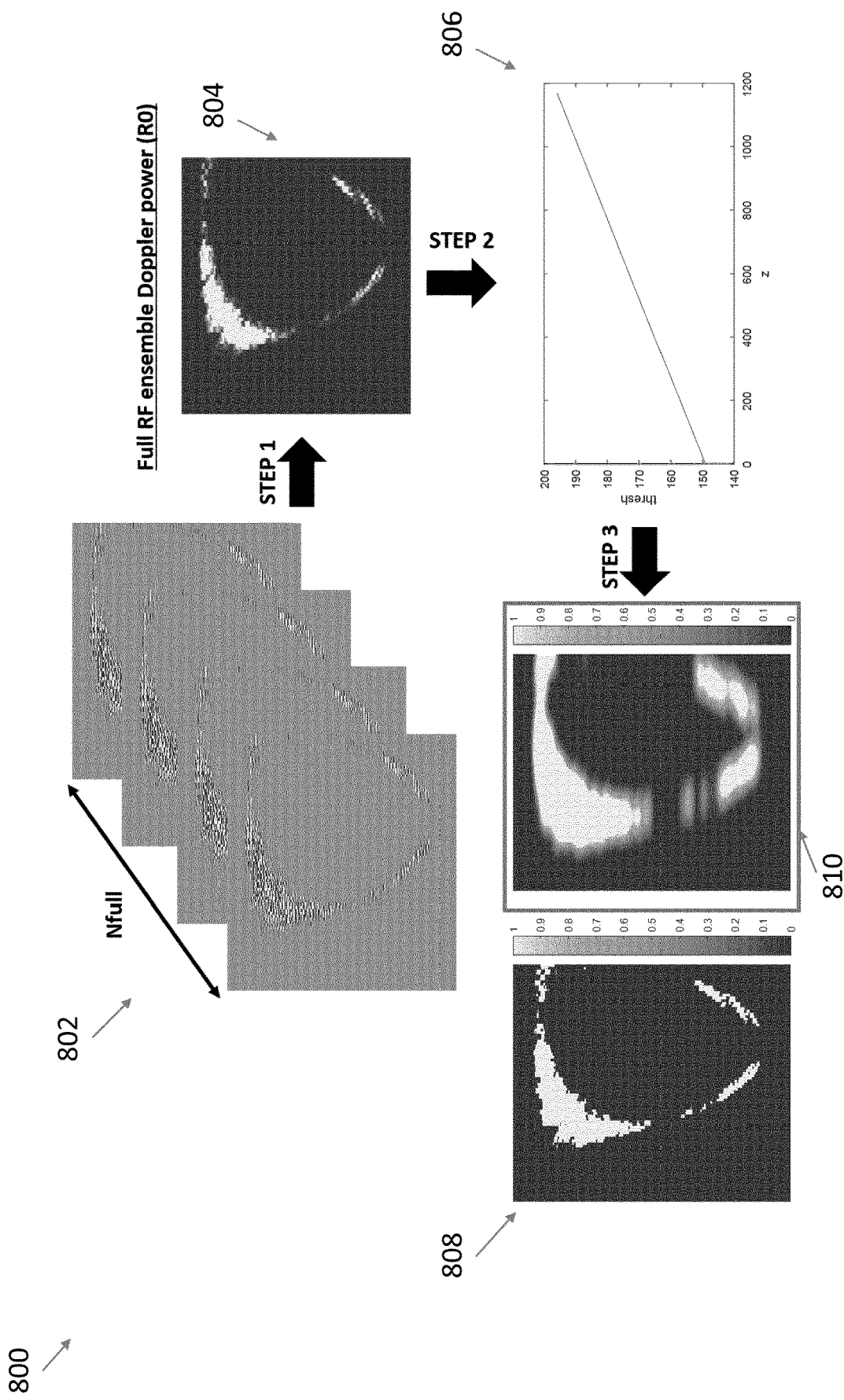
FIG. 8 is a flowchart of a method that illustrates use of optional masked loss in accordance with the principles of the present disclosure.

FIG. 8 is a flowchart of a method 800 that illustrates use of optional masked loss in accordance with the principles of the present disclosure. As discussed in reference to FIG. 7, masking the mean squared loss may help ensure that a neural network, such as neural network 700, learns to reconstruct meaningful flow areas while avoiding biases from high magnitude Doppler phase noise (e.g., from surrounding tissue without flow). Equation 2 provides the MSE loss:

$$\text{Loss}(R_1) = E[(\text{Mask} \cdot (R_{1_{pred}} - R_{1_{true}}))^2] \quad \text{Equation 2}$$

Where E is the expected value/mean and R1 is the lag-1 autocorrelation function for the RF ensemble (e.g., Doppler phase). $R1_{pred}$ is the Doppler phase image predicted by the neural network and $R1_{true}$ is the high-quality Doppler phase image generated from the long and/or high PRF RF-ensemble. Mask is the mask generated using the R0 (lag-0) power Doppler image from the long and/or high PRF RF-ensemble.

FIG. 8 illustrates the steps to generate the mask in Equation 2 for when the neural network is trained on post-wall-filtered data. A post-wall filtered long and/or high PRF RF-ensemble 802 of N frames is acquired and a Doppler power (R0) image 804 is estimated from the long and/or high PRF ensemble 802 as provided by:

$$R0(x,z) = \Sigma_{i=1}^{N} |RF_{wallfiltered}(x,z,i)|^2 \quad \text{Equation 3}$$

Where $RF_{wallfiltered}(x,z,i)$ is the long wall-filtered ensemble, x is the azimuth coordinate, z is depth and i is the index in the RF-ensemble.

A linear depth-dependent threshold 806 is also estimated for the mask as given by:

$$\text{threshold}(z) = a \cdot z + \frac{E[R0]}{K} \quad \text{Equation 4}$$

Where $\alpha$ and K are user-defined parameters that define how aggressive the threshold is, and E[R0] is the mean of the long and/or high PRF ensemble R0. Finally, an estimated (e.g., raw) mask 808 and a smoothed mask 810 are generated by the equations:

$$\text{Mask}_{raw}(x, z) = \begin{cases} 1, & R0(x, z) \geq \text{threshold} \\ 0, & R0(x, z) < \text{threshold} \end{cases} \quad \text{Equation 5}$$

$$\text{Mask}(x, z) = G(x, z) * \text{Mask}_{raw}(x, z) \quad \text{Equation 6}$$

Where G(x, z) indicates a Gaussian kernel and asterisk (*) indicates convolution. The method shown in Equations 5 and 6 are only an example. Other more advanced/complex thresholding strategies could be followed to obtain the Mask and other filtering kernels, methodologies could be used as well.

A mask, such as mask 808 or mask 810 or a mask generated using another suitable process is supplied to a neural network, such as neural network 700, during training. In the example shown in FIG. 7, the mask 808 or mask 810 may be provided to the neural network 700 as indicated by arrow 710. As discussed with reference to FIG. 7, the mask found as shown in FIG. 8 is used only during training for loss estimation with the long and/or high PRF RF-ensemble is available. During deployment, the neural network has already been trained. Thus, the mask is no longer needed since no loss estimation or training takes place (except in embodiments where dynamic training is employed). In some examples, the same mask may be used to detect flow areas and generate image patches that include flow for training data sets to train the neural network. This may be similar to obtaining image patches that are centered around pixels where mask(x, z)>0.

When the adversarial loss from a discriminator network, discussed with reference to FIG. 7 and Equation 1, is also used, the total loss given by:

$$\text{Loss}_{advers} = \frac{1}{2}(R1 \text{ loss} - \left(-\sum(\text{label}_i \cdot \log(p(\text{label}_i)) + (1 - \text{label}_i) \cdot \log(1 - p(\text{label}_i))))\right) \quad \text{Equation 7}$$

Where R1 loss is provided by Equation 2. Thus, the neural network may be trained to minimize the masked loss and maximize the discriminator loss. In other words, the neural network may be trained to ignore noise and render the discriminator network unable to discriminate between the long RF ensemble CD images and the enhanced CD images generated by the neural network.

While examples of the present disclosure have been described with reference to CD images, at least some of the principles of the present disclosure may be applied to power Doppler (PD) images (e.g., R0, lag-0 autocorrelation). For example, a neural network, such as neural network 700, or an additional branch of the neural network, may be used to generate enhanced PD images from short and/or undersampled RF ensembles to mimic PD images generated from long and/or high PRF ensembles. In these examples, a standard loss (e.g., mean squared error loss) and/or a masked loss (e.g., as provided in Equation 2) may be used when training the neural network to generate enhanced PD images. In some examples, a logarithmic loss may be applied, which may facilitate optimization of the neural network by compressing the arithmetic values involved. The logarithmic loss may be given by:

$$\text{Loss}(R_0) = E[(\log(1+R_{0_{pred}}) - \log(1+R_{0_{true}}))^2] \quad \text{Equation 8}$$

Where E indicates the expected value/mean and R0 is the lag-0 autocorrelation function for the RF ensemble (e.g., power Doppler information). $R0_{pred}$ is the Doppler phase image predicted by the neural network and $R0_{true}$ is the high-quality Doppler phase image generated from the long and/or high PRF RF-ensemble.

Figure 9:
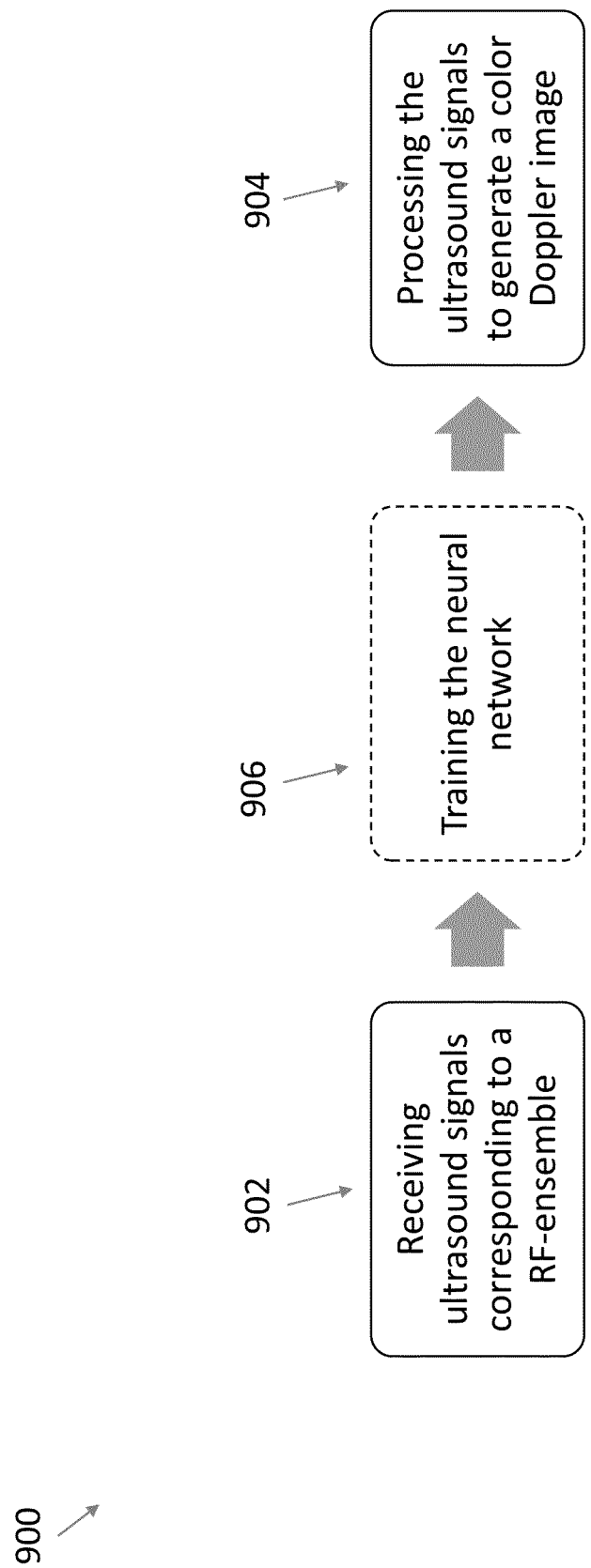
FIG. 9 is a flow chart of a method in accordance with the principles of the present disclosure.

FIG. 9 is a flow chart of a method 900 in accordance with the principles of the present disclosure. In some examples, the method 800 may be performed by an ultrasound imaging system, such as system 200 shown in FIG. 2. In some examples, method 900 may be performed by a Doppler processor, such as Doppler processor 260.

At block 902, "receiving ultrasound signals corresponding to a RF-ensemble" may be performed. The receiving may be performed by a processor, such as Doppler processor 260. The RF-ensemble may have a first length (e.g., a number of pulses, RF-frames), a first pulse repetition frequency (PRF), and/or a first sensitivity. The RF-ensemble may have been transmitted by an ultrasound probe, such as ultrasound probe 212. The ultrasound signals resulting from the RF-ensemble may have been received by the ultrasound probe and the signals provided to the processor.

At block 904, "processing the ultrasound signals to generate a color Doppler image" may be performed. The processing may be performed by the processor. In some examples, processing may include estimating a second RF-ensemble from the first RF-ensemble based, at least in part, on reference ultrasound signals that correspond to at least one reference RF-ensemble. The reference RF-ensemble may have at least one of a second pulse repetition rate, a second length, or a second sensitivity different than the first RF-ensemble. Processing may also include generating a color Doppler image using the second RF-ensemble. In some examples, the enhanced color Doppler image may have at least one of a sensitivity or a velocity estimate (e.g., estimates of blood flow velocities) closer to a color Doppler image generated from a RF-ensemble having characteristics similar to the reference RF-ensemble than a color Doppler image generated from the RF-ensemble without processing. In some examples, the reference RF-ensemble may have a length greater than the RF-ensemble. That is, the second length may be greater than the first length. For example, the second length may be a length corresponding to a long ensemble (e.g., ~14 frames) whereas the first length corresponds to a short and/or undersampled ensemble (e.g., ~4 frames). In some examples, the processing may be performed by a neural network. In some examples, the neural network may be a series of convolutional networks, such as two uNets as shown in FIG. 7.

Optionally, at block 906, "training the neural network" may be performed in examples where the processing is performed by a neural network. In some examples, training may include providing a plurality signals corresponding to RF-ensembles having the first length as inputs and providing a corresponding plurality of color Doppler images generated from a corresponding plurality of signals corresponding to RF-ensembles of the second length as desired outputs. In some examples, the inputs may be generated by subsets of the RF-ensembles of the second length. The training sets may be acquired from simulations, flow phantoms, and/or in vivo. In some examples, masking and/or adversarial losses may be applied during training. In some examples, the neural network is trained prior to being implemented (e.g., deployed) on the processor.

Figure 10:
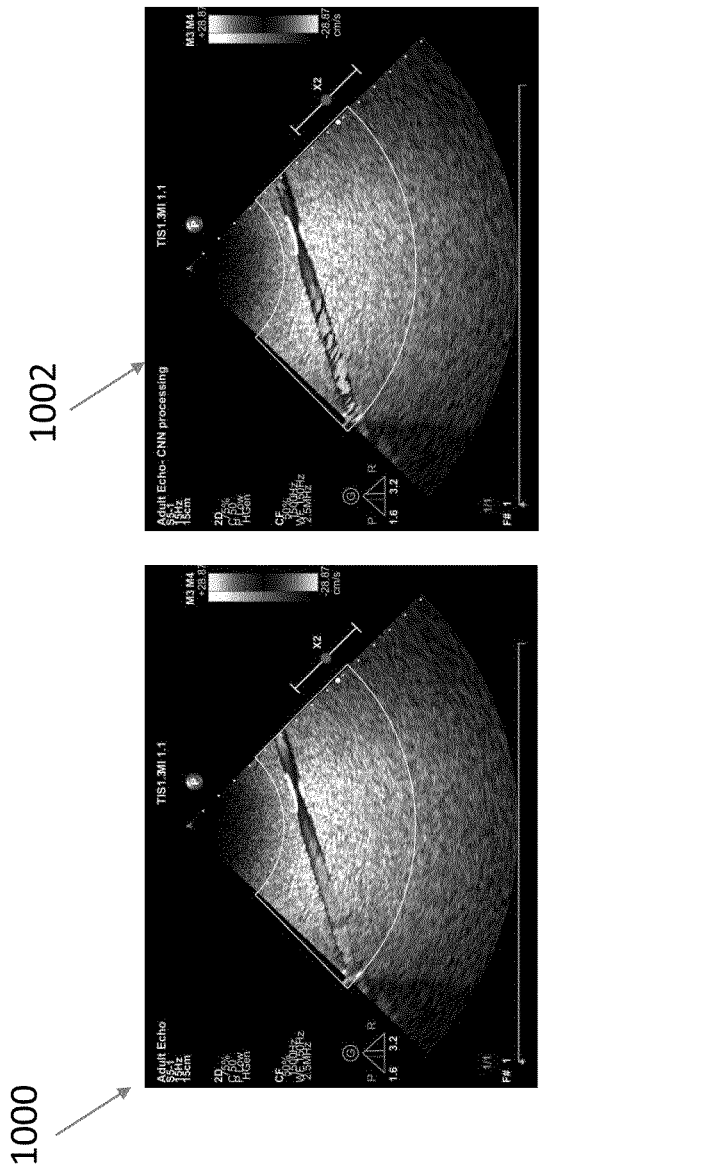
FIG. 10 shows an example decimated ensemble color Doppler image and an example enhanced color Doppler image in accordance with the principles of the present disclosure.

FIG. 10 shows an example decimated ensemble color Doppler image 1000 and an example enhanced color Doppler image 1002 in accordance with the principles of the present disclosure. The image 1000 was acquired from a Gammex flow phantom acquired using an EPIQ system (Philips Healthcare). In this example, the neural network used to generate the enhanced CD image 1002 was trained only on simulation datasets (e.g., from Field II). Despite the neural network only being trained on simulation data, the enhanced CD image 1002 of the flow phantom exhibits partial compensation of the aliasing of velocity estimates present in the decimated ensemble CD image 1000.

Figure 11:
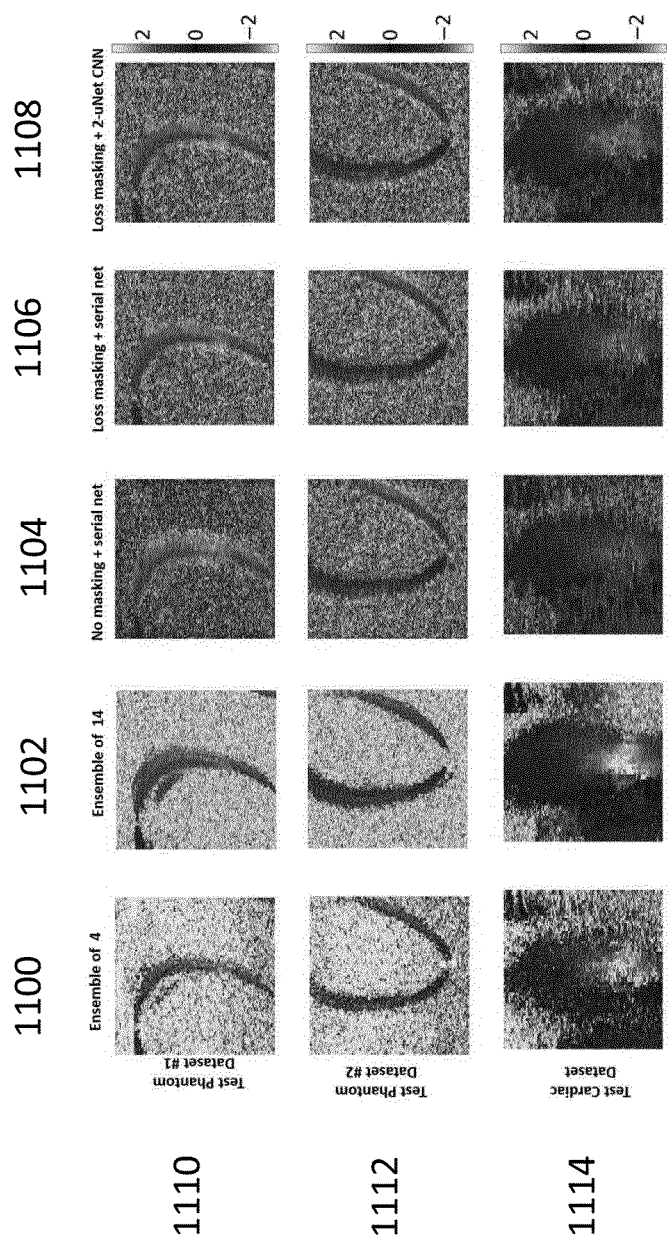
FIG. 11 shows example short ensemble, long ensemble, and enhanced raw phase shift result color Doppler images in accordance with the principles of the present disclosure.

FIG. 11 shows example short ensemble, long ensemble, and enhanced raw phase shift result color Doppler images in accordance with the principles of the present disclosure. Column 1100 includes CD images from a decimated ensemble of four frames. Column 1102 includes CD images from a long ensemble of 14 frames. Column 1104 includes enhanced CD images generated by a series of conventional CNNs with no masking applied during training. Column 1106 includes enhanced CD images generated by a series of conventional CNNs with masking applied during training. Column 1108 includes enhanced CD images generated by the neural network 700 shown in FIG. 7 with the masking applied during training. All of the neural networks were trained solely on phantom data for this example. Images in row 1110 were acquired from a first Gammex flow phantom. Images in row 1112 were acquired from a second Gammex flow phantom. Images in row 1114 are cardiac images acquired in vivo. Moving right from column 1104 to column 1108, for each of the imaged media (e.g., the first Gammex flow phantom, the second Gammex flow phantom, and the in vivo subject) shown in each of the three rows 1110, 1112 and 1114, respectively, gradual improvements in the enhanced CD images (e.g., noise suppression, resolution) can be seen.

Figure 12:
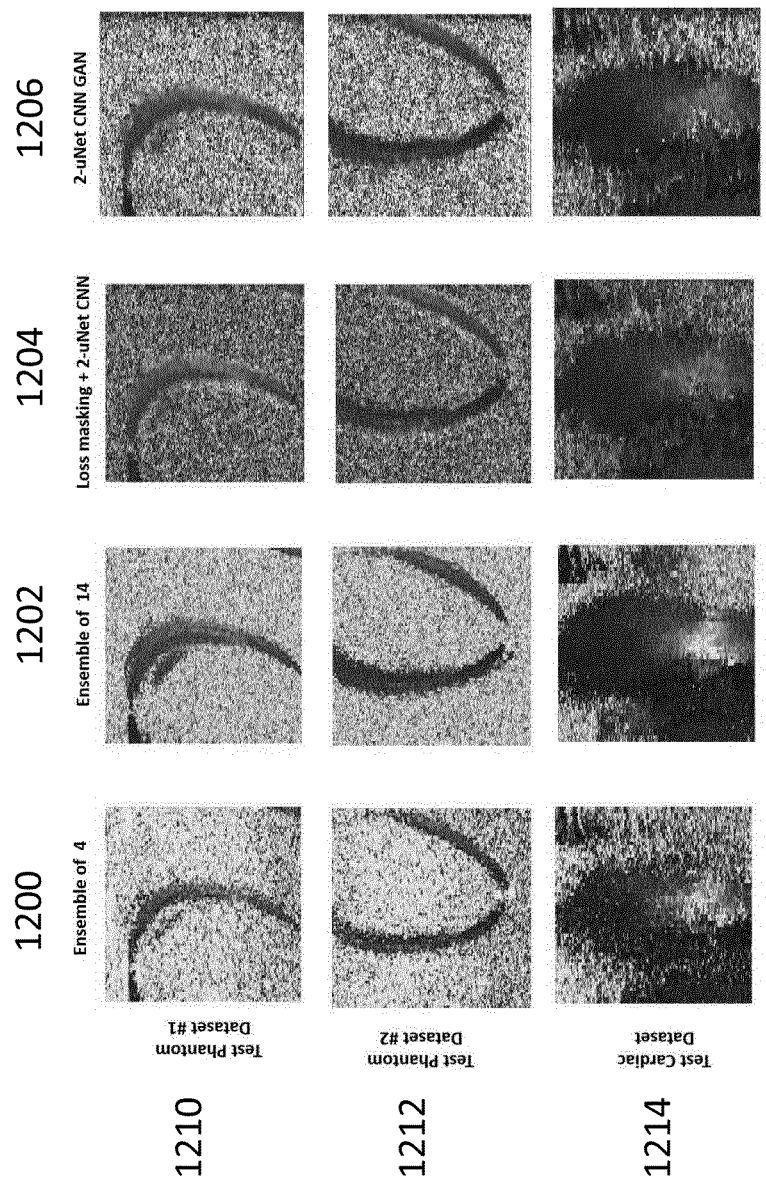
FIG. 12 shows example short ensemble, long ensemble, and enhanced raw phase shift result color Doppler images in accordance with the principles of the present disclosure.

FIG. 12 shows example short ensemble, long ensemble, and enhanced raw phase shift result color Doppler images in accordance with the principles of the present disclosure. Column 1200 includes CD images from a decimated ensemble of four frames. Column 1202 includes CD images from a long ensemble of 14 frames. Column 1204 includes enhanced CD images generated by the neural network 700 shown in FIG. 7 with the masking applied during training. Column 1206 includes enhanced CD images generated by the neural network 700 shown in FIG. 7 with the masking and adversarial loss applied during training. All of the neural networks were trained solely on phantom data for this example. Images in row 1210 were acquired from a first Gammex flow phantom. Images in row 1212 were acquired from a second Gammex flow phantom. Images in row 1214 are cardiac images acquired in vivo. Moving right from column 1204 to column 1206, improvements in the enhanced CD images (e.g., noise suppression, resolution) can be seen.

Figure 13:
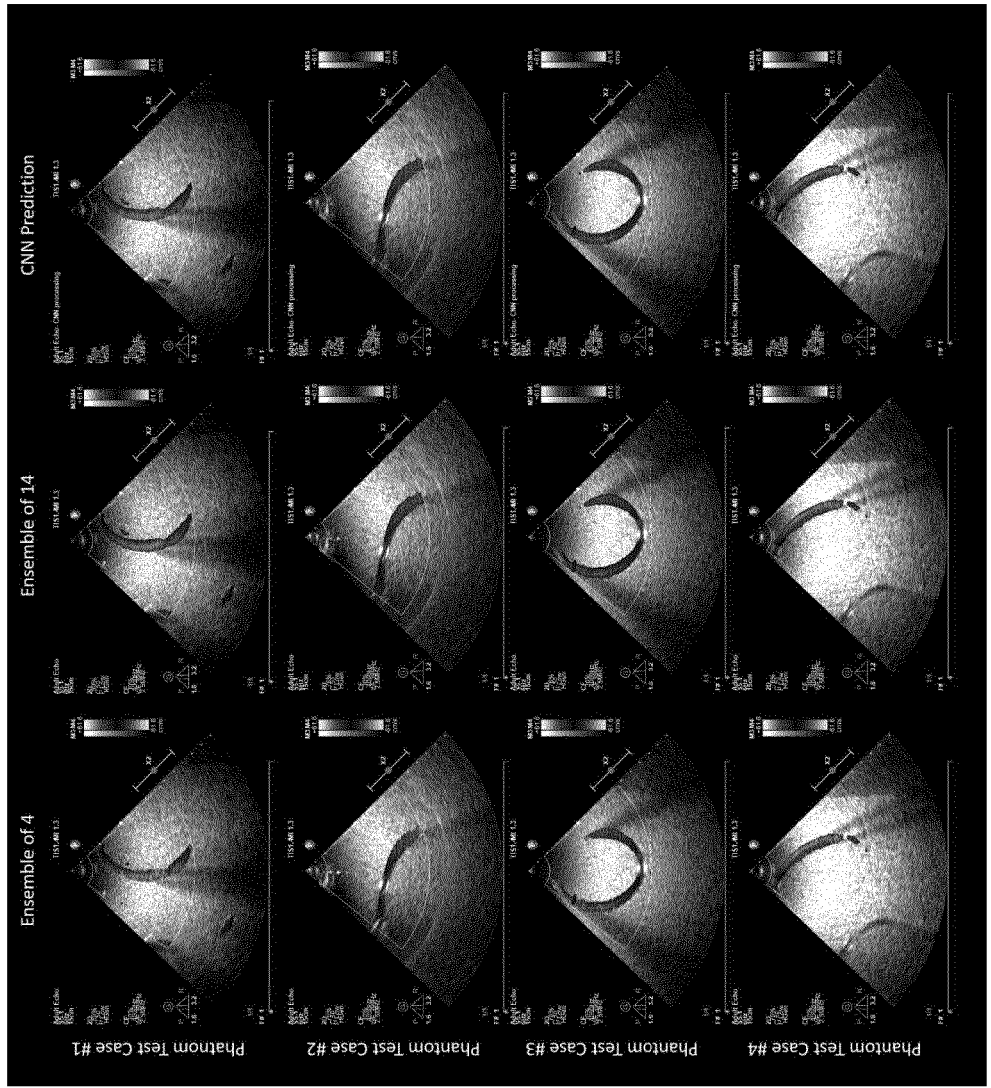
FIG. 13 shows example short ensemble, long ensemble, and enhanced post-processed color Doppler images in accordance with the principles of the present disclosure.

FIG. 13 shows example short ensemble, long ensemble, and enhanced post-processed color Doppler images in accordance with the principles of the present disclosure. Column 1300 includes CD images from an ensemble of four frames for four different Gammex flow phantoms. Column 1302 includes CD images from a long ensemble of 14 frames for the four different Gammex flow phantoms. Column 1304 includes enhanced CD images generated by the neural network 700 shown in FIG. 7 with the masking applied (but no adversarial loss) during training for the four different Gammex flow phantoms. The neural network 700 was trained solely on phantom data for this example. The images shown in column 1304 are more similar to the images of column 1302 than the images shown in column 1300, indicating that the neural network 700 may provide enhanced CD images from short and/or undersampled ensembles with improved sensitivity, velocity estimates, and/or resolution compared to unprocessed short and/or undersampled ensembles.

Figure 14:
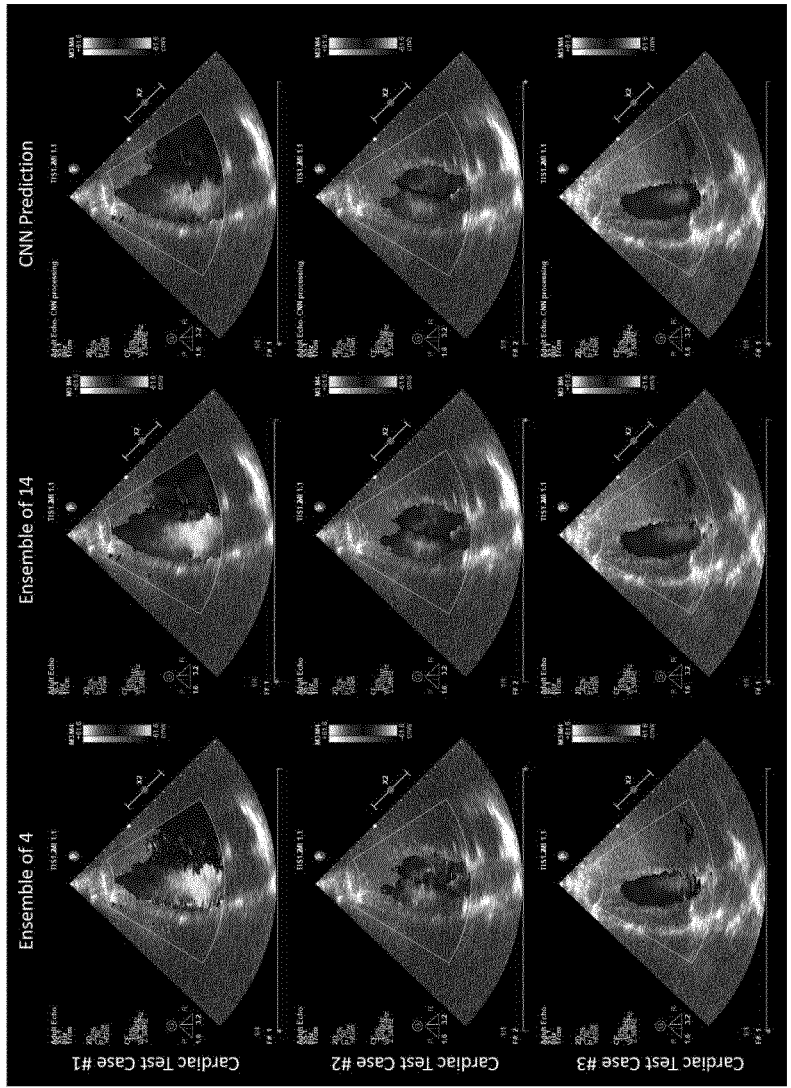
FIG. 14 shows example short ensemble, long ensemble, and enhanced post-processed color Doppler images in accordance with the principles of the present disclosure.

FIG. 14 shows example short ensemble, long ensemble, and enhanced post-processed color Doppler images in accordance with the principles of the present disclosure. Column 1400 includes CD images from an ensemble of four frames for three different cardiac test cases acquired in vivo. Column 1402 includes CD images from a long ensemble of 14 frames for the three different cardiac test cases acquired in vivo. Column 1204 includes enhanced CD images generated by the neural network 700 shown in FIG. 7 with the masking applied (but no adversarial loss) during training for the three different cardiac test cases acquired in vivo. The neural network 700 was trained solely on phantom data for this example. The images shown in column 1404 exhibit reduced flow velocity variance and greater noise suppression compared to the images shown in column 1400, indicating that the neural network 700 may provide enhanced CD images from short and/or undersampled ensembles with improved sensitivity, velocity estimates, and/or resolution compared to unprocessed short and/or undersampled ensembles. Further improvements may be seen by training neural network 700 on in vivo training datasets rather than phantom ones or increasing the flow velocities in the phantom datasets to match velocities in cardiac flows.

All of the example results shown in FIGS. 9-13 used the power Doppler (R0) of the full ensemble to ensure fair comparison of the estimated flow velocities. This means that the mask used to determine whether to show the Color Doppler (R1) or the B-mode image at a specific pixel was derived from the full ensemble.

As disclosed herein, artificial intelligence (e.g., deep learning) may be leveraged to link short and/or undersampled ensembles to CD images generated using longer ensembles. More specifically, a deep learning framework including one or more convolutional neural networks (CNN), such as two serial uNets may be used to process short and/or undersampled ensembles to generate CD images mimicking those generated from longer ensembles. During training, the deep learning framework may receive short and/or decimated ensembles as input data and CD images generated from long and/or high PRF ensembles as desired output data. Once trained, the deep learning framework may provide enhanced CD images from short and/or undersampled ensembles that are higher quality (e.g., higher sensitivity, more accurate velocity estimations) compared to typical CD images generated from short and/or undersampled ensembles. In other words, the enhanced CD images provided by the deep learning framework may provide CD images closer to the quality of CD images generated from long and/or high PRF ensembles. In some applications, the systems and methods disclosed herein may provide improved CD images with less loss of frame rate and/or interleaving capabilities.

Although the examples described herein discuss processing of ultrasound image data, it is understood that the principles of the present disclosure are not limited to ultrasound and may be applied to image data from other modalities such as magnetic resonance imaging and computed tomography.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "C #", "Java", "Python", and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
a processor configured to:
receive ultrasound signals corresponding to a first radiofrequency (RF) ensemble comprising a first length, a first pulse repetition frequency (PRF), and a first sensitivity;
estimate a second RF-ensemble from the first RF-ensemble based, at least in part, on reference ultrasound signals that correspond to at least one reference RF-ensemble comprising at least one of a second pulse repetition rate, a second length, or a second sensitivity different than the first RF-ensemble; and
generate a color Doppler image using the second RF-ensemble,
wherein the processor implements a neural network to estimate the second RF-ensemble,
wherein the neural network comprises a series of convolutional neural networks,
and further wherein the neural network further generates the color Doppler image, and wherein a first neural network of the series of convolutional neural networks receives the ultrasound signals corresponding to the RF-ensemble and provides a mean Doppler phase image and a Doppler phase as a first output, wherein a second neural network of the series of convolutional neural networks receives the first output and provides the color Doppler image as a second output.

2. The ultrasound imaging system of claim 1, wherein the processor is further configured to wall-filter the ultrasound signals corresponding to the first RF-ensemble.

3. The ultrasound imaging system of claim 1, wherein the series of convolutional neural networks are uNets.

4. A method comprising:
receiving ultrasound signals corresponding to a first radiofrequency (RF) ensemble comprising a first length, a first pulse repetition frequency (PRF), and a first sensitivity;
estimating a second RF-ensemble from the first RF-ensemble based, at least in part, on reference ultrasound signals that correspond to at least one reference RF-ensemble comprising at least one of a second pulse repetition rate, a second length, or a second sensitivity different than the first RF-ensemble, wherein the estimating is performed by a neural network comprising a series of convolutional networks, wherein the neural network is trained by;
providing at least one RF-ensemble having at least one of a third length, a third PRF, or a third sensitivity that is the same as the first RF-ensemble; and providing a corresponding color Doppler image generated from the reference RF-ensemble as a desired output; and generating a color Doppler image using the second RF-ensemble.

5. The method of claim 4, further comprising wall-filtering the ultrasound signals prior to the estimating.

6. The method of claim 4, further comprising generating a plurality of reference RF-ensembles from subsets of the at least one reference RF-ensemble.

7. The method of claim 4, wherein the input and the desired output are acquired from at least one of a flow phantom, a simulation, or in vivo.

8. The method of claim 4, wherein the training further comprises applying a masked mean squared error (MSE) loss.

9. The method of claim 8, wherein the masked MSE loss is based, at least in part, on power Doppler data of the reference RF-ensemble.

10. The method of claim 4, wherein the training further comprises applying an adversarial loss.

11. The method of claim 10, wherein the adversarial loss is based on a binary cross-entropy loss generated by training a discriminator network to distinguish color Doppler images generated from the first RF-ensemble from color Doppler images generated from the reference RF-ensemble.

12. The method of claim 11, wherein the discriminator network has a conditional generative adversarial network architecture.

13. The method of claim 4, wherein the first RF-ensemble and the reference RF-ensemble are wall-filtered.

14. The method of claim 4, wherein the first RF-ensemble comprises an undersampled ensemble.

15. The method of claim 4, further comprising processing the first RF-ensemble with the neural network or a second neural network to generate a first power Doppler image, based at least in part, on the at least one reference RF-ensemble.

16. A non-transitory computer-readable medium comprising instructions, that when executed, causes an imaging system to:

receive ultrasound signals corresponding to a first radiofrequency (RF) ensemble comprising a first length, a first pulse repetition frequency (PRF), and a first sensitivity;

estimate a second RF-ensemble from the first RF-ensemble based, at least in part, on reference ultrasound signals that correspond to at least one reference RF-ensemble comprising at least one of a second pulse repetition rate, a second length, or a second sensitivity different than the first RF-ensemble, wherein the estimating is performed by a neural network comprising a series of convolutional networks, wherein the neural network is trained by;

providing at least one RF-ensemble having at least one of a third length, a third PRF, or a third sensitivity that is the same as the first RF-ensemble; and providing a corresponding color Doppler image generated from the reference RF-ensemble as a desired output; and generate a color Doppler image using the second RF-ensemble.

* * * * *